United States Patent [19]

Murray et al.

[11] Patent Number: 5,495,541
[45] Date of Patent: Feb. 27, 1996

[54] OPTICAL DELIVERY DEVICE WITH HIGH NUMERICAL APERTURE CURVED WAVEGUIDE

[76] Inventors: Steven C. Murray, 1536 San Antonio St., Menlo Park, Calif. 94025; Donald M. McPherson, 6018 Colby St., Oakland, Calif. 94623

[21] Appl. No.: 229,598

[22] Filed: Apr. 19, 1994

[51] Int. Cl.[6] .................................................. G02B 6/321
[52] U.S. Cl. ........................... 385/33; 385/117; 385/902; 606/17; 600/101
[58] Field of Search ........................ 606/17; 128/4; 385/117, 33, 902, 115, 32, 31

[56] References Cited

U.S. PATENT DOCUMENTS

| | | | |
|---|---|---|---|
| 4,076,377 | 2/1978 | Moraschetti | 350/96.25 |
| 4,503,853 | 3/1985 | Ota et al. | 128/303.1 |
| 4,538,609 | 9/1985 | Tanenaka et al. | 128/303.1 |
| 4,576,147 | 3/1986 | Hashiguchi | 128/6 |
| 4,592,353 | 6/1986 | Daikuzono | 128/303.1 |
| 4,736,743 | 4/1988 | Daikuzono | 128/303.1 |
| 4,740,047 | 4/1988 | Abe et al. | 350/96.15 |
| 4,787,689 | 11/1988 | Korotky et al. | 350/96.12 |
| 5,037,174 | 8/1991 | Thompson | 385/33 |
| 5,042,980 | 8/1991 | Baker et al. | 606/194 |
| 5,078,711 | 1/1992 | Kakami et al. | 606/16 |
| 5,100,507 | 3/1992 | Cholewa et al. | 156/651 |
| 5,129,897 | 7/1992 | Daikuzono | 606/13 |
| 5,154,708 | 10/1992 | Long et al. | 606/16 |
| 5,164,945 | 11/1992 | Long et al. | 372/6 |
| 5,207,669 | 5/1993 | Baker et al. | 606/7 |
| 5,221,279 | 6/1993 | Cook et al. | 606/15 |
| 5,257,991 | 11/1993 | Fletcher et al. | 606/17 |
| 5,267,995 | 12/1993 | Doiron et al. | 606/15 |
| 5,274,227 | 12/1993 | Moring | 385/32 |
| 5,371,826 | 12/1994 | Friedman | 385/115 |
| 5,394,492 | 2/1995 | Hwang | 385/33 |

FOREIGN PATENT DOCUMENTS 0069351  7/1981  European Pat. Off. ........ A61B 17/36

*Primary Examiner*—John D. Lee
*Assistant Examiner*—Phan T. H. Palmer
*Attorney, Agent, or Firm*—Haynes & Davis

[57] ABSTRACT

An optical delivery device includes an optical fiber that receives an output beam of light from a light source such as a laser. The optical fiber includes a linear section, defining a longitudinal axis, and a curved distal end, with a curvature sufficient so that total internal reflection of the light around a bend is maintained and bending losses within the curved distal end are minimized. The curved distal end has a distal output tip that delivers substantially all of the output beam in a defined lateral direction from the longitudinal axis. The numerical aperture of the curved distal end is larger than the numerical aperture of the light in the linear section. The numerical aperture of the curved distal end can be increased by removing the fiber cladding and replacing it with a lower index material. By placing the curved distal end in a hollow sealed tube the fiber is effectively clad with a material of refractive index similar to 1, which creates a very high numerical aperture curved waveguide structure and allows very small curvatures to be made without bending losses.

31 Claims, 7 Drawing Sheets

OPTICAL DELIVERY DEVICE WITH HIGH NUMERICAL APERTURE CURVED WAVEGUIDE

FIELD OF THE INVENTION

This invention relates generally to optical delivery devices, and more particularly to optical delivery devices that deliver an output beam of light in a lateral direction with a curved waveguide structure.

BACKGROUND OF THE INVENTION

It has been found useful to employ optical delivery devices that include optical fibers and deliver an output beam of light in a direction that is generally lateral with respect to the longitudinal axis of the optical fiber. In particular, this type of delivery device has found wide acceptance in minimally invasive medical applications, including but not limited to the treatment of benign prostatic hyperplasia.

One method of laterally directing light in a fiber optic is to use a prism or a metal or dielectric mirror tilted with respect to the fiber optic longitudinal axis. There are several geometric and thermal limitations to this method. The mirror angle must be sufficiently obtuse, and its distance from the fiber optic sufficiently large enough to minimize the reflected light which passes through the side of the optic. Additionally, the mirror must be large with respect to the fiber diameter and be encased in a protective tube with a window which results in additional fresnel losses. This reflected light can cause undesirable heating of adjacent tissue and can make the aim beam difficult to visualize.

Metal mirrors have low reflectance, less than 95%, and this results in heat generation which limits their use to low power applications. Although high reflectance dielectric mirrors do not generate heat, they suffer from the same inherent geometric problems.

Another method of angularly directing light is to reflect the light from the beveled surface of a fiber tip. The beveled fiber surface totally internally reflects the light when it is in contact with a medium of sufficiently low refractive index. This is the most common technique presently used and is described in U.S. Pat. Nos. 4,740,047 and 5,257,991 Alternatively, the beveled surface can be coated with a reflective metal or dielectric stack. The problem with beveled fibers is that the light reflecting off the beveled face strikes the highly curved surface of the fiber. Rays that strike the periphery of the fiber at glancing incidence are reflected back, leading to low transmission and unacceptable levels of back scattered light. Another problem is that the light passing through the side of the fiber is subject to a very short focal length cylindrical lens, which causes the light to sharply focus and diverge in one dimension.

Although refraction can be used to divert the light, it has certain limitations. For example, it is limited to diverting the light at small angles. Additionally, there are significant reflection losses unless an anti-reflective coating is applied to the beveled surface.

One of the simplest ways of laterally directing light is to bend the optical fiber. However, when the fiber is sharply bent, light escapes along the outer portion of the bend. To prevent these bending losses, the radius of curvature must be so large, greater than 20 times the fiber diameter, that they cannot be used for endoscopic procedures where space is at a premium.

There is a need for an optical delivery device that laterally directs light in a fiber optic to a desired site without causing undesirable heating of adjacent tissue, and without making an aim beam difficult to visualize. Such optical delivery devices are particularly useful in high power applications and produce a minimum of scattered light.

SUMMARY OF THE INVENTION

An object of the invention is to provide an optical delivery device that delivers an output beam of light in a direction laterally in relation to the longitudinal axis of an optical fiber.

Another object of the invention is to provide an optical delivery device that delivers an output beam of light laterally without heating material not directly irradiated.

Yet another object of the invention is to provide an optical delivery device that delivers an output beam of light in a lateral direction and produces a minimum of scattered light which can interfere with visualization.

Still a further object of the invention is to provide an optical delivery device that laterally delivers an output beam of light with a curved waveguide structure.

Another object of the invention is to provide an optical delivery device that laterally delivers an output beam of light with a curved waveguide structure that has a bend, and a radius of curvature that is sufficient so that total internal reflection of light around the bend is maintained.

These and other objects are achieved in an optical delivery system that includes a light source which produces an output beam of light. An optical fiber is coupled to the light source with an output beam. The optical fiber includes a generally linear section with a longitudinal axis, and a curved distal end. The curved distal end is bent with sufficient curvature so that total internal reflection of the light around the bend is maintained. A distal output tip is defined as the end of the curved distal end where light emerges. Substantially all of the output beam is delivered in a defined lateral direction from the longitudinal axis, enabling the light to be precisely delivered. By minimizing the bending losses, scattered light does not interfere with visualization or heat adjacent tissue.

With the optical delivery device of the present invention, the curved distal end has a numerical aperture that is greater than a numerical aperture of light in the linear section of the optical fiber. The curved distal end has a diameter D, an index of refraction $n_2$ at the curved distal end, and the curved distal end is surrounded by a media having an index of refraction $n_3$. Because high NA light in an optical fiber totally internally reflects (TIR) from a core/cladding interface at steeper angles than the less divergent low NA light, it is the first light to leak out when the fiber is bent. In order to minimize bending losses over the curve, it is required that the highest NA light in the fiber be totally internally reflected at the core-cladding interface. For total internal reflection to be maintained in the curved fiber, the angle $\psi$ between a ray of the highest NA light and a line perpendicular to the tangent of the curve must fulfill the following relationship:

$$\psi = \sin^{-1}(n_3/n_2)$$

Where
$\psi$=The angle the highest NA light strikes a line perpendicular to the tangent to the curve.
$n_2$=The refractive index of the curved waveguide core.

$n_3$ = The refractive index of the material surrounding the curved waveguide.

The NA of the light in a fiber is given by NA=Sin σ, where σ is the angle of the most divergent light makes with a line perpendicular to the fiber surface. The NA of the light ($NA_L$) in the fiber is distinguished from the NA of the fiber ($NA_F$). $NA_F$ of a step index fiber is given by $NA_F = \sqrt{n_2^2 n_{cl}^2}$, where $n_2$=the refractive index of the fiber core, and $n_{CL}$=the refractive index of the fiber cladding. The NA of the fiber represents the most divergent light that propagates down the fiber optic. When $NA_F$ and $NA_L$ are equal, any curvature of the fiber causes bending losses. Typically when fiber optics are used, $NA_F$ and $NA_L$ are similar. Consequently, when the fibers are sharply bent, bending losses result.

To prevent such bending losses when the fiber is sharply bent, the NA of the light entering the bend must have a lower NA than the NA of the curved portion of the fiber. The present invention discloses several ways of accomplishing this, and various types of curves which allow the light to be directed laterally with little or no bending losses.

In one embodiment of the invention, the optical delivery device includes a cannula. The optical fiber is positioned in at least partially within the cannula. At least a portion of the curved distal end of the fiber is outside of the cannula. Surrounding the curved distal end is a hollow cap that attaches to the distal end of the cannula and to the distal end of the linear section of the optical fiber. Preferably, the interior space of the hollow cap is filled with a gas or a vacuum, so that the curved distal end is surrounded by as low an index material as possible. The distal output tip is fused to an interior wall of the cap. Additionally, for a transparent hollow cap, it is desirable if the hollow cap and curved distal end are made of the same material or a material with the same thermal expansion coefficient and refractive index.

For most devices it is critical that the total transmission device be as high as possible. To prevent the various problems which result when the transmission of the device is low, it is useful to understand the most common loss mechanisms, their consequences and methods of minimizing them. These loss mechanisms are:

1) When light is coupled from the light source to the fiber, there are fresnel reflections from the air/fiber interface. These reflective losses typically are about 4 to 10%, depending on the refractive index of the fiber core and the numerical aperture of the light. Because the light is simply reflected back at the light source, these losses do not cause problems at the distal end of the probe.

2) A variety of loss mechanisms are possible in the linear fiber. However, over short distances these losses are minuscule in commercially available fiber optics.

3) If the linear fiber section and curved waveguide are separate pieces, fresnel reflections can occur at the junction. These reflective losses can be reduced by anti-reflection coating the two surfaces, using an index matching material, or by thermally fusing them together.

4) Scattering losses can occur at the interface of the curved waveguide core and the material surrounding it, if the waveguide does not have an optically smooth surface. These losses can be reduced by not scratching the curved waveguide and keeping it clean.

5) If the curved waveguide is placed in contact with a transparent window or the inside of a capillary tube, reflections from the fiber/air or air/window interface occur. These reflections are reflected back into the curved waveguide. After the light makes a sharp bend, its numerical aperture distribution increases. When this high NA light is reflected into the bend, it can leak out of the bend, which was designed for lower NA light. Even though this light is usually only a few percent, it can make an aim beam difficult to visualize. This loss can be eliminated by fusing the distal tip of the fiber with a window or capillary tube of the same material. Another method is to have the curved fiber protrude from a hole in the side of the cap.

6) Similar reflections occur from reflections when the light exits the device. These reflection are less than 1% when the light enters water, but can be several percent if the probe is in air. These reflections in air can be greatly reduced by anti-reflecting coatings or by index matching materials.

The present invention provides for greatly reducing and eliminating bending losses in a curved waveguide.

DETAILED DESCRIPTION OF THE PREFERRED EMBODIMENTS

Figure 1A:
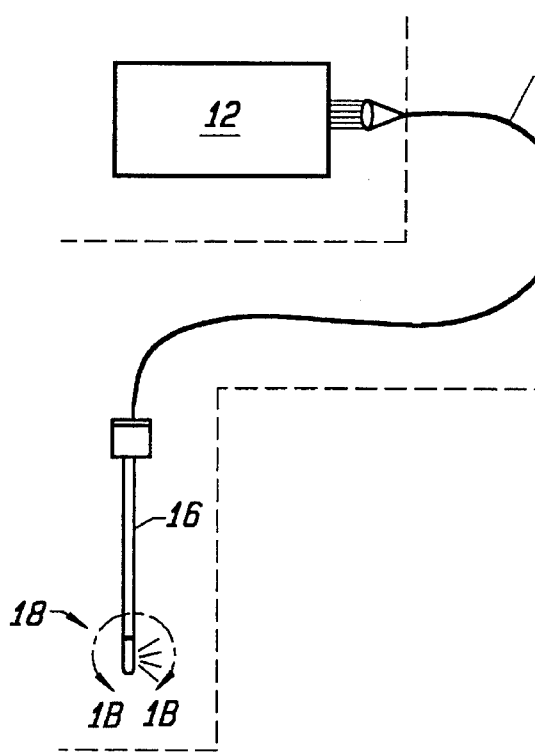
FIG. 1(A) is a schematic diagram of an optical delivery system with an optical energy source, and an optical delivery system.
Figure 1B:
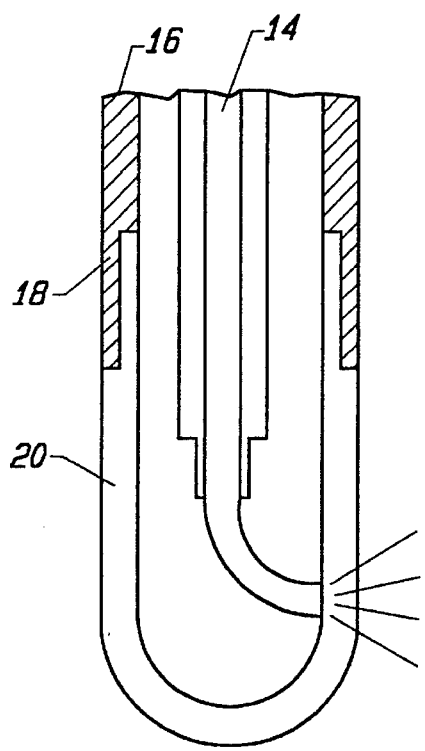
FIG. 1(B) is a cross sectional view of the distal end of optical delivery system of FIG. 1(A).

FIGS. 1(A) and 1(B) illustrate an optical delivery system 10, including an optical light source 12, an optical fiber 14 coupled to receive an output beam of light from optical light source 12, and a cannula 16 that houses optical fiber 14.

Optical fiber 14 extends beyond a distal end 18 of cannula 16. Attached to either optical fiber 14 or to the distal end 18 of cannula 16 is a hollow cap 20. Cannula 16 can be a rigid tube or the lumen of an endoscope. Optical light source 12 can be a laser, including but not limited to an Nd:YAG dual wavelength laser operating at 533 nm or 1064 nm, a solid state laser based on holmium thulium or erbium, a dye laser, or an incoherent light source.

Figure 2:
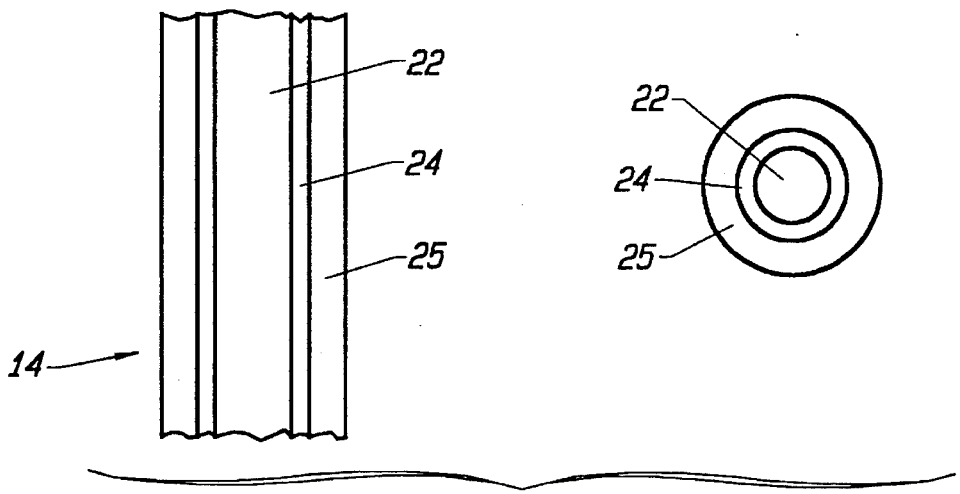
FIG. 2 is a cross sectional view of an optical fiber.

FIG. 2 shows optical fiber 14 with a core 22, a cladding 24 surrounding the optical fiber core 22, and a buffer coating 25 that surrounds cladding 24. Optical fiber 14 may be made of any material that transmits an optical output of light. Suitable materials include glass, quartz, crystals and plastics, including but not limited to polymethylmethacralate (PMMA), polycarbonate and certain liquids. Optical fiber 14 has practically no size limitation. Preferred sizes are in the range of 100 to 1000 microns.

Ordinarily, when an optical fiber is bent in a tight radius of curvature, light propagating down the fiber will escape the fiber, If, however, the numerical aperture of a curved portion of the optical fiber is larger than the numerical aperture of the light entering the optical fiber, or curved waveguide, there will be a critical radius of curvature for which total internal reflection is still maintained.

Figure 3:
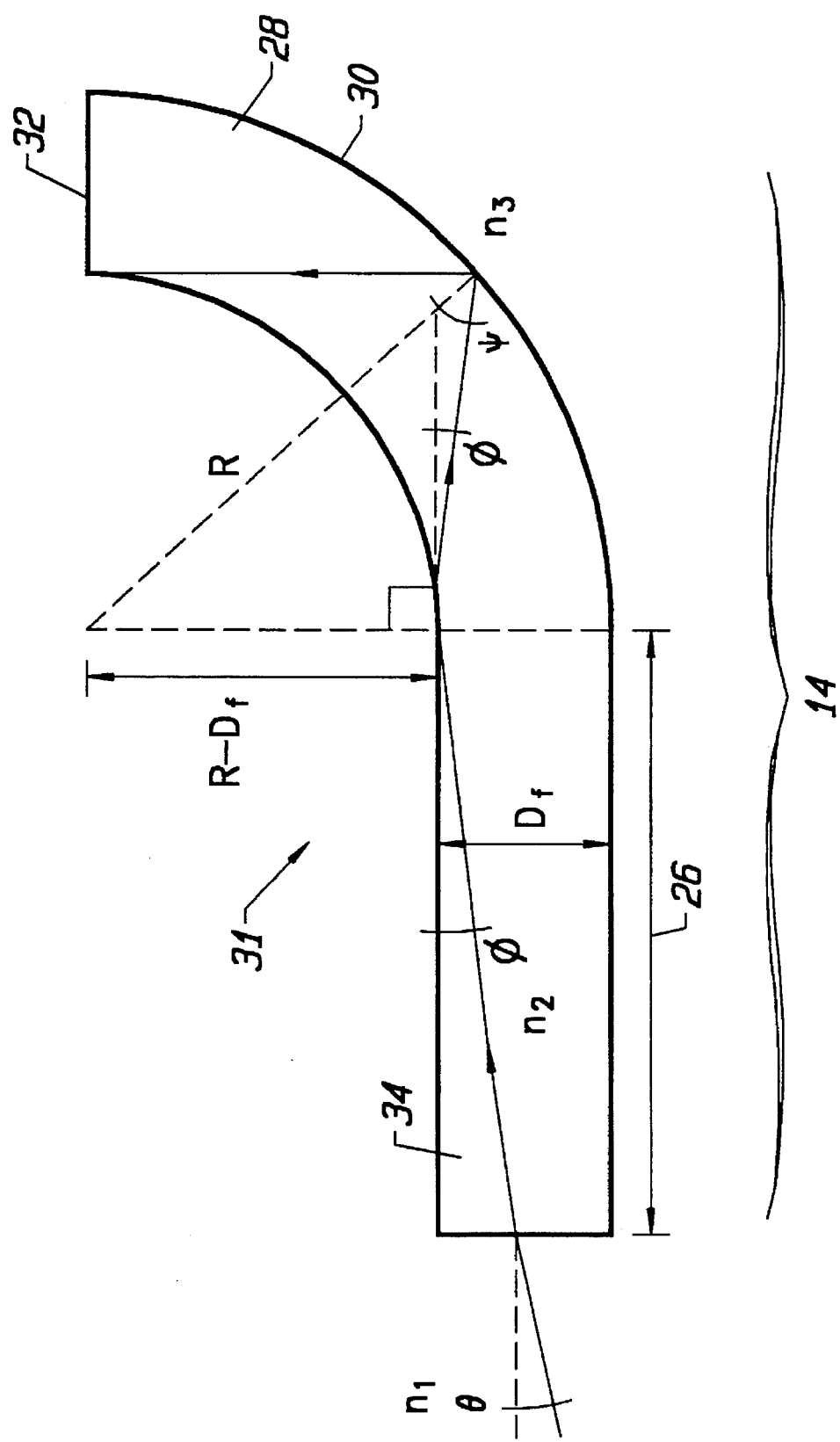
FIG. 3 is a cross sectional view of an optical fiber illustrating the reflection of a light ray in a linear section of the fiber, and the curved distal end.

FIG. 3 illustrates an embodiment of the present invention where optical fiber 14 has a linear section 26, and a curved distal end 28 with a toroidal bend 30 in curved distal end 28. For purposes of this disclosure, linear section 26 and curved distal end 28 are collectively referred to as a curved waveguide 31. Light exits from optical fiber 14 laterally from a generally longitudinal axis of optical fiber 14, the longitudinal axis of linear section 26, through a distal output tip 32.

The bending losses can be kept below 1% and the light reflected from distal output tip 32 can be kept below 6% in air, and less than 1% in water. There is very little light lost through reflections or other loss mechanisms. In air, all but 10%, and in water all but 5% of the output beam is delivered in the defined lateral direction.

For purposes of the present invention, curvature means substantially torodial or spherical, and can include parabolic, elliptical, hyperbola, and combinations thereof.

FIG. 3 shows that light 34 traveling down fiber optic 14 has a numerical aperture distribution. The most divergent light traveling down optical fiber 14 has the highest numerical aperture. This high numerical aperture light propagates down linear section 26, totally internally reflecting off an optical fiber core/cladding interface. This most divergent light strikes curved distal end 28 of optical fiber 14 at a more acute angle than the light rays of lower numerical aperture. As optical fiber 14 is bent, this angle decreases until the condition for total internal reflection is no longer satisfied. As long as the most divergent light totally internally reflects off the outermost bend 30 in optical fiber 14, all of the lower numerical aperture light is also transmitted without loss around bend 30. As previously mentioned, a variety of curved waveguides 31 can be used to laterally direct the light. One of the simplest to calculate and manufacture is a toroidal curve. For a tordial curve, there is a simple formula for the minimum bend radius optical fiber 14 can have before bending losses occur.

The following definitions and equations are used in determining the minimum bend radius of a torodial curve.

$n_1$=The refractive index of air $\approx 1$.
$n_2$=The refractive index of curved distal end 28 core.
$n_3$=The refractive index of the material surrounding the curved distal end 28.
D=The diameter of fiber 14.
R=The radius of curvature measured to the outside of bend 30.
$\sigma$=The angle of light incident on linear fiber core 28.
$\phi$=The angle of light refracted into the linear fiber core 28.
$\psi$=The angle the highest NA Light strikes a line perpendicular to the surface of bend 30.
$NA_L$=Sin $\sigma$=the numerical aperture of light 34 entering linear fiber section 26.
$NA_F$=The maximum numerical aperture of light 34 linear section 26 can transmit.

To determine the minimum bend radius R, the most divergent light ray 34 enters linear section 26 at some $NA_L$ less than or equal to the numerical aperture of linear section 28. Light ray 34 strikes linear section 28 core at an angle $\theta$ and refracts at an internal angle $\theta$. This ray propagates down optical fiber 14 without its NA changing significantly.

The high NA light strikes a line perpendicular to bend 30 in optical fiber at an angle $\psi$. In order for this light to totally internally reflect from the cladding of optical fiber 14, the following condition must be met:

$$\psi \geq \sin^{-1}[n_3/n_2] \qquad \text{Equation (1)}$$

This condition allows a calculation of the minimum radius R that optical fiber 14 can be bent before bending losses occur. This dependence is given in $$R \geq D.\{1/[1-\sin\psi/\cos\theta]\} \qquad \text{Equation (2)}$$

where $$\cos\phi = \sqrt{[1-(NA/n_2)^2]} \qquad \text{Equation (3)}$$

The following expression results from combining these relationships and simplifying them:

$$R \geq \frac{Dn_2\sqrt{1-(NA/n_2)^2}}{n_2\sqrt{1-(NA/n_2)^2} - n_3} \qquad \text{Equation (4)}$$

Figure 4:
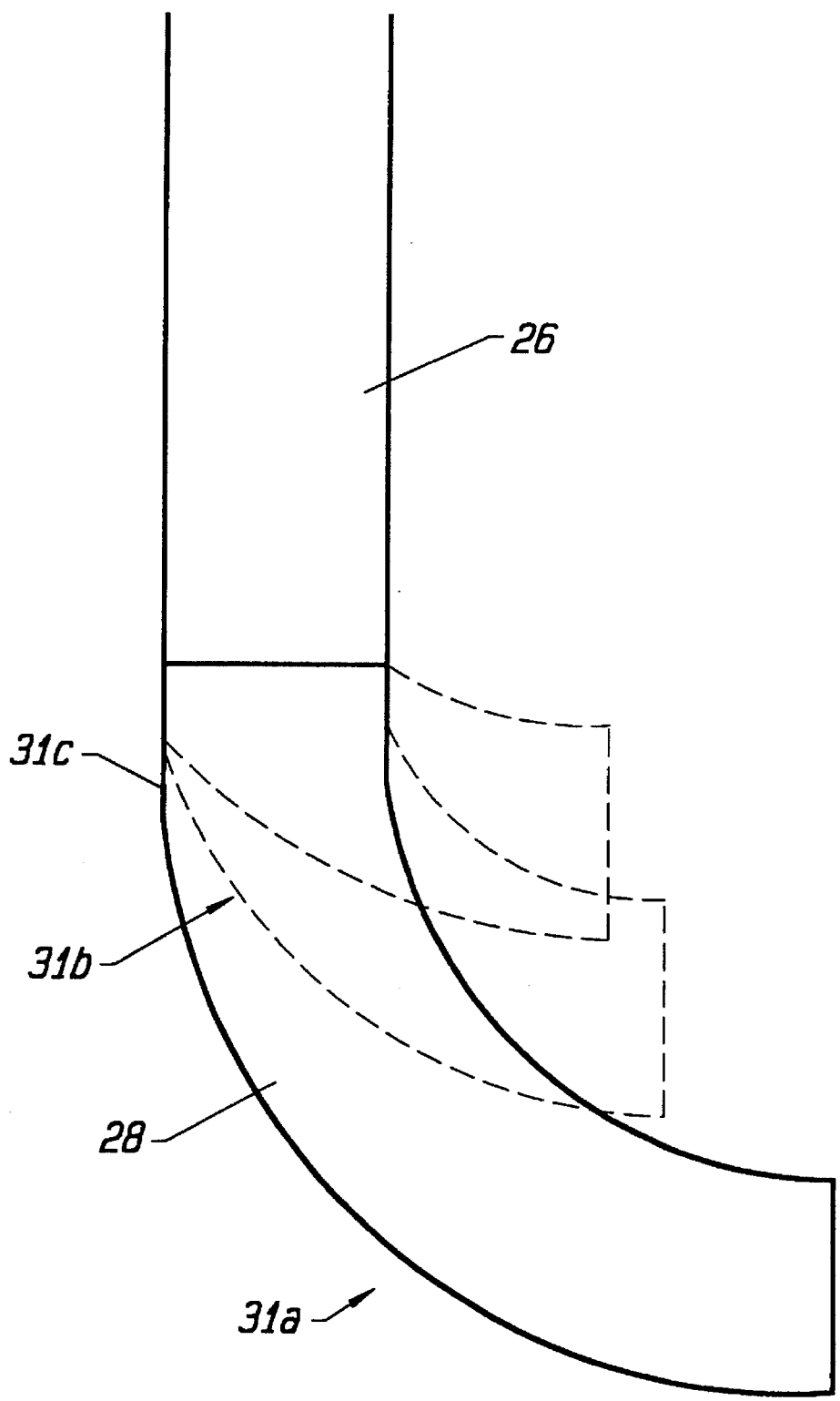
FIG. 4 illustrates a toroidally curved fiber compared to an elliptically and parabolically or spherical curved fiber, all of which laterally direct the light at 90 degrees, but could be designed to direct the light at angles greater than or less than 90 degrees.

A more complicated relationship can be derived for any shaped curve as long as the light strikes a perpendicular to the tangent line of the curve at an angle $\psi$. FIG. 4 shows examples of toroidal 31a, elliptical 31b, and parabolic 31c curved waveguides 31 which direct the light 90 degrees with respect to the linear fiber axis. As optical fiber 14 is bent with a radius of curvature less than R, the high NA light will leak out. In some instances, when small size is more important than transmission, this may be desirable. Optical fiber 14 can always have a larger radius of curvature. This increases the size of the optical delivery device, and in some instances it may be easier to manufacture. Although FIG. 3 shows optical fiber 14 bent at 90 degrees, it can be, if desired, diverted less than or more than 90 degrees.

Table 1 lists 24 examples of the minimum radii of curvature which will not produce bend losses for different fiber diameters, NA light, refractive index $n_2$ of the curved distal end 28, and refractive index $n_3$ of the material surrounding curved distal end 28.

TABLE 1

|   | R(mm) | NA | $N_2$ | $N_3$ | Dmm |
|---|-------|-----|-----|-----|-----|
| 1 | 0.611 |     |     |     | 0.2 |
| 2 | 0.916 |     |     |     | 0.3 |
| 3 | 1.22  | 0.2 | 1.5 | 1   | 0.4 |
| 4 | 1.83  |     |     |     | 0.6 |
| 5 | 3.06  |     |     |     | 1   |

TABLE 1-continued

| | R(mm) | NA | $N_2$ | $N_3$ | Dmm |
|---|---|---|---|---|---|
| 6 | 1.2 | 0 | | | |
| 7 | 1.22 | 0.2 | | | |
| 8 | 1.3 | 0.4 | 1.5 | 1 | 0.4 |
| 9 | 1.47 | 0.6 | | | |
| 10 | 3.81 | 1 | | | |
| 11 | | | | 1 | |
| 12 | 1.81 | | | 1.3 | |
| 13 | 1.22 | | | 1.5 | |
| 14 | 1.08 | 0.2 | 1.6 | 1 | 0.4 |
| 15 | 0.98 | | 1.7 | | |
| 16 | 0.91 | | 1.8 | | |
| 17 | 1.22 | | | 1 | |
| 18 | 2.5 | | | 1.3 | |
| 19 | 5.28 | 0.2 | 1.5 | 1.4 | 0.4 |
| 20 | | | | 1.5 | |
| 21 | 1.74 | 0.2 | | 1.3 | |
| 22 | 3.59 | | 1 | 1.5 | 0.4 |
| 23 | 1.46 | 0.2 | 1.8 | 1.3 | |
| 24 | 2.48 | | 1.8 | 1.5 | |

A number of valuable embodiments can be seen from the bend radius formula of Equation (4).

Figure 5:
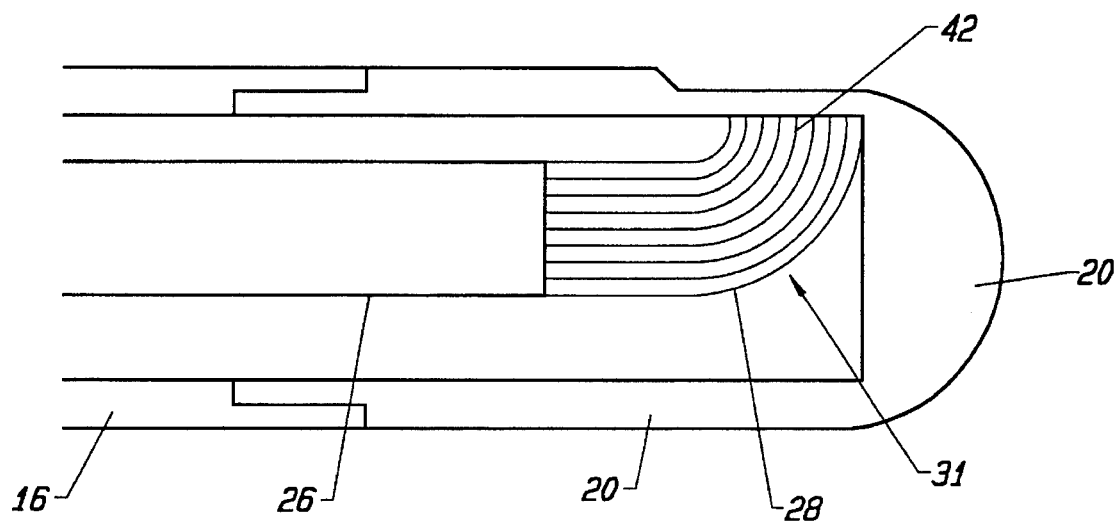
FIG. 5 illustrates a curved waveguide made from a fiber bundle.

As shown in FIG. 5, because the minimum bent radius is directly proportional to the fiber diameter, smaller fibers allow sharper bends. Alternatively, a fiber bundle can be used for achieving sharp bend radii. Although fiber bundles are extensively used to transmit light, they are used because they provide greater flexibility than a solid core fiber of the same diameter. The minimum bend radius achievable with a bundle is determined by applying a bend radius condition of the present invention to the fibers on the inside bend in the bundle. Most fiber bundles break if they are bent as sharply as the formula of Equation (4) implies; however, as with a single core fiber, the bundle can be thermally bent. This is particularly easy if the bundle is a rigid glass clad bundle.

Figure 6:
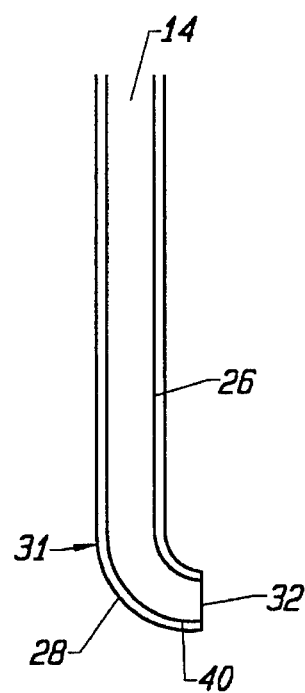
FIG. 6 illustrates a high NA curved waveguide with low NA light, allowing a low index solid or liquid to clad the curved waveguide.

In FIG. 6, another embodiment of the invention relies on coupling low NA light into a high NA linear fiber section 26. Over short lengths, essentially none of light 14 is coupled to more divergent higher order modes. Because curved distal end 28 has a high NA, the light does not leak out of fiber 14 unless fiber 14 is bent too sharply. This method has the advantage of not needing to surround the curved distal end 28, with a gas in order to provide a high NA curved waveguide 31. Consequently, the need for hollow protective cap 20 is eliminated. For high NA glass clad fibers, the coating is striped, the fiber thermally bent and the protective coating reapplied. For plastic clad fibers, both the coating is stripped off, the fiber thermally bent, the fiber cladding can be reapplied or alternatively a lower index cladding can be used. After curved waveguide 31 is re-clad, a protective coating is applied.

Figure 7:
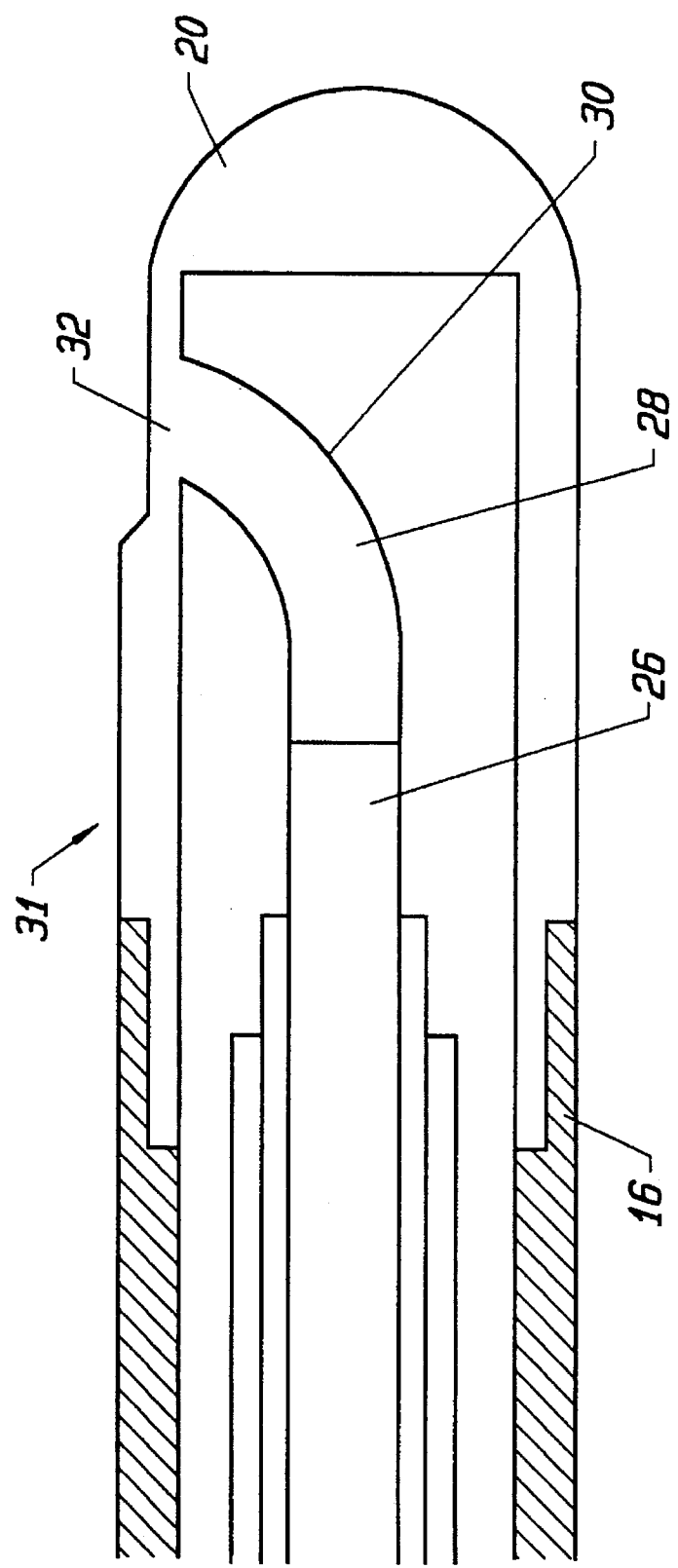
FIG. 7 is a cross sectional view of an optical delivery device. The linear section of the optical fiber and the curved distal end are two separate pieces.

Another embodiment of the present invention, is to thermally bend, mold or grind and polish a waveguide to the desired shape. This has a higher refractive index than a linear fiber and is spliced to the linear fiber and surrounded with a material of low refractive index. The spliced embodiment is illustrated in FIG. 7.

It will be appreciated that the present invention extends beyond step index fibers and curved waveguides. The present invention is suitable for graded index fibers with curved distal ends 28. The NA of curved distal end 28 needs to be higher than the NA of the light in linear fiber section 26. Thus, the present invention includes GRIN fibers with curved distal ends 28. Additionally, linear fiber cross section 26 and curved distal end 28 need not be cylindrical.

Figure 8A:
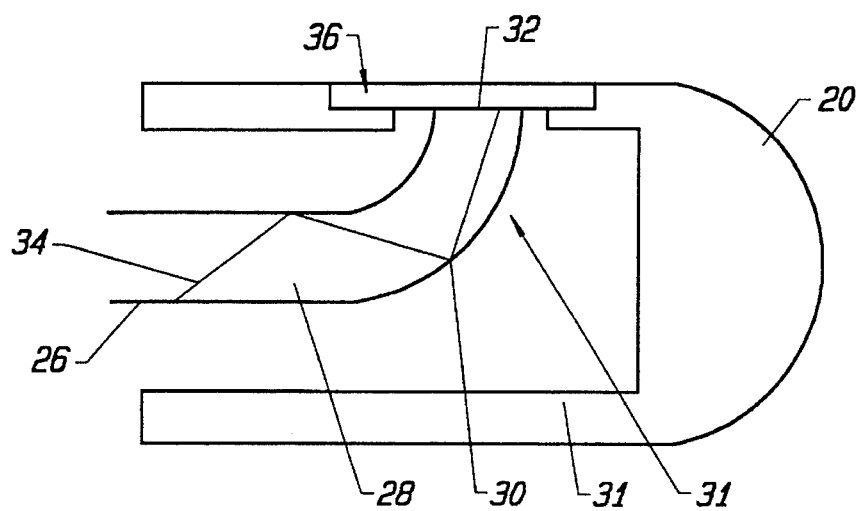
FIG. 8(A) is a sectional view of a cannula with a window and an output tip of the curved distal end of an optical fiber attached to the window.
Figure 8B:
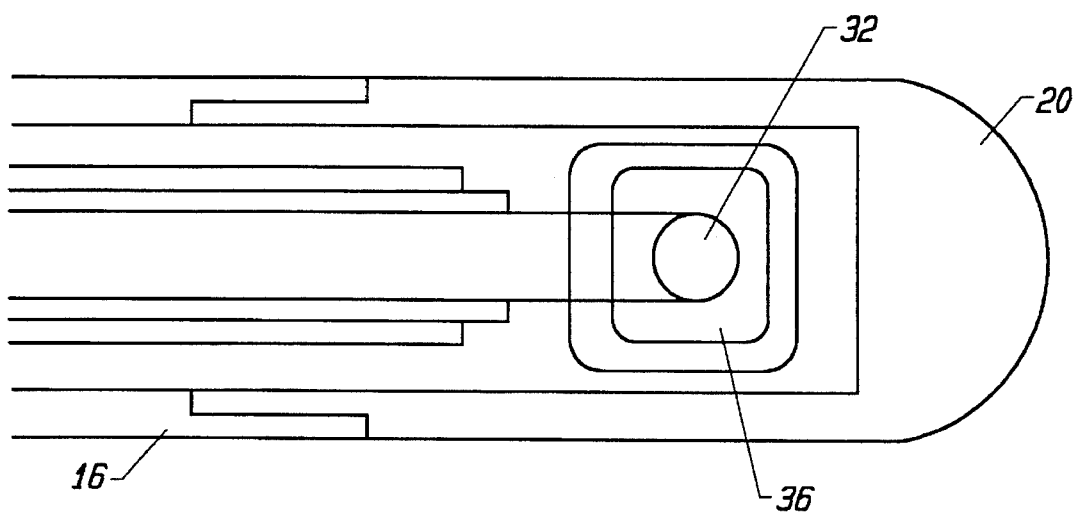
FIG. 8(B) is a top view of a cannula with a window and an output tip of the curved distal end of an optical fiber attached to the window.

After light 34 reflects from curved distal 28, some of light 34 is coupled into higher order more divergent modes. In other words the NA of light 34 is increased by the bend. Light reflected from distal output 32 tip, window 36 (FIG. 8(A) and (B)), or hollow cap 20 is be reflected back into the curved waveguide 31. If bend 30 has been designed to have the smallest possible radius of curvature for the low NA light, some of this higher NA reflected light will escape from bend 30. To alleviate this problem, the radius of curvature can be increased to accommodate this higher NA light. Because this increases the size of the device, it is preferable to reduce the reflections as much as possible. These reflections can be reduced by keeping the number of surfaces to a minimum, and by anti-reflection coating and/or index matching them. This is the principle reason why it is desirable to fuse the distal tip of the curved waveguide to a window or a the inside of the capillary tube. In air approximately 5% of the light will be reflected back into curved waveguide 31 and a only a small fraction of which will escape through bend 30. In water the reflections are less than 1% and can be ignored.

Figure 9:
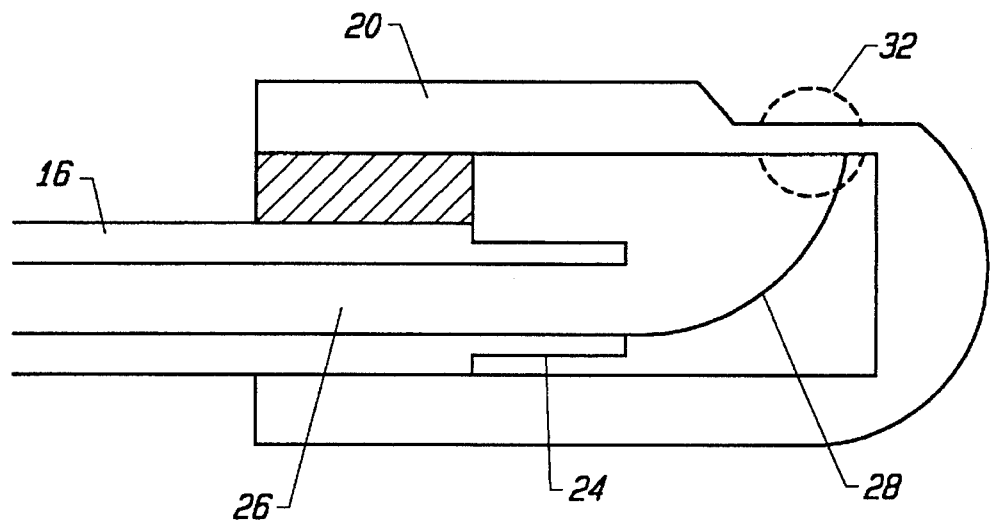
FIG. 9 is a cross sectional view of an optical delivery device that employs an optical fiber having a linear section, a curved distal end of the optical fiber, and a hollow cap attached to a distal end of the linear section, with an interior wall of the cap being fused to an output tip of the curved distal end.

In the preferred embodiments of the invention, a glass core plastic clad multimode step index fiber is used, as shown in FIG. 9. Fiber buffer coating (not shown) and cladding 24 are mechanically, chemically, or thermally removed from fiber 14. This region normally extends a few millimeters from curved distal end 28 of fiber 14. Optical fiber 14 is then thermally bent, preferably 90 degrees, using preferably a laser, an electric arc, or a torch. The bend can be precisely controlled by using a mechanical force or gravity or the surface tension of thermally softened fiber 14 or any combination of these forces. Optical fiber 14 is then trimmed to the required length using a cleaver, a precision saw, or by using precision grinding equipment.

In one preferred embodiment, a closed end hollow cap 20 is slid over the curved tip of the fiber as shown in FIG. 9. The outside faces of hollow cap 20 where curved distal tip 28 of curved waveguide 31 are adjacent to each other can be ground flat. Hollow cap 20 can also be frosted or anti reflection coated to minimize unwanted reflections. The distal end tip 32 is placed in contact with the inner wall of hollow cap 20, and then thermally fused together by a laser, an electric arc or a torch. By fusing distal end tip 32 of curved waveguide 31 to the inside of hollow cap 20, optical fiber 14 is held securely in place and the 10% reflective losses at the fiber/air and air/hollow cap 20 interface are eliminated. Hollow cap 20 can contain air, gas, a vacuum or various other media of low refractive index. Air is preferred. Fiber 14 is then sealed to fiber 14 on the linear portion of the fiber 14 using adhesives.

Figure 10:
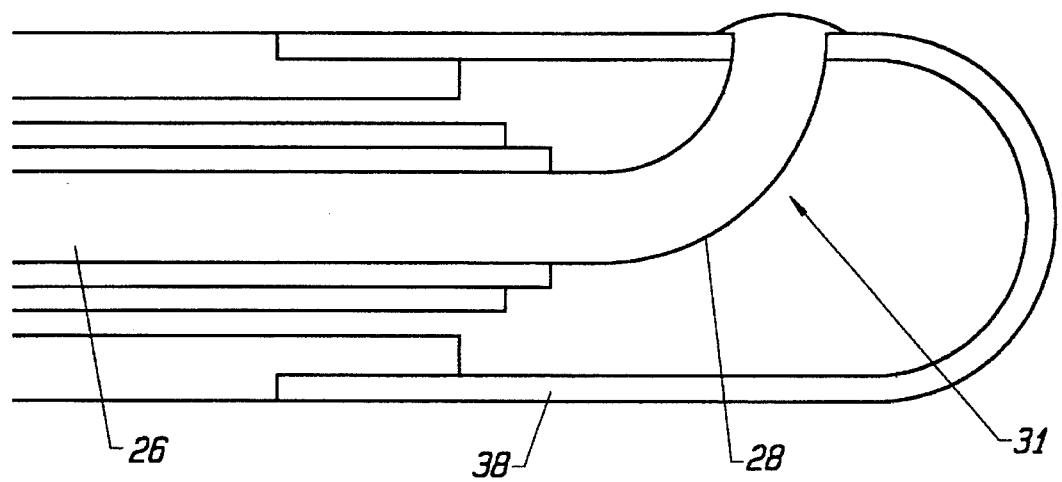
FIG. 10 illustrates a metal cap with a hole for the distal tip of the curved waveguide to protrude.

In another preferred embodiment, a metal tube, preferably made from a platinum alloy is used instead of a glass hollow cap 20. In this embodiment, illustrated in FIG. 10, a metal tube 38 is sealed at one end and a hole is made in the side of the tube for curved waveguide 31 to fit through. After curved distal end 28 of curved waveguide 31 has been placed through tube 38, it is thermally melted and fused to the outside of metal tube 38. Adhesive is then used to seal metal tube 38 to linear section 26 of fiber 14.

Additionally, in FIG. 6, a high NA curved waveguide 31, with low NA light, includes a low index solid or liquid 40 to clad curved waveguide 31.

Changes and modifications in the specifically described embodiments can be carried out without departing from the scope of the invention which is intended to be limited only by the scope of the appended claims.

What is claimed:

1. An optical delivery system, comprising:
   a light source producing an output beam of light;

an optical fiber coupled to the light source to receive the output beam of light, the optical fiber including a linear section defining a longitudinal axis, and a curved distal end having a bend with a numerical aperture that is 0.2 or greater than a numerical aperture of the output beam entering the curved distal end, the curved distal end having a distal output tip that delivers substantially all of the output beam in a defined lateral direction from the longitudinal axis.

2. The optical delivery system of claim 1, wherein the light source is a laser.

3. The optical delivery system of claim 1, wherein the light source is an incoherent light source.

4. The optical delivery system of claim 1, wherein the curved distal end has a toroidal shape with a radius of curvature R given by:

$$R \geq \frac{Dn_2 \sqrt{1-(NA/n_2)^2}}{n_2 \sqrt{1-(NA/n_2)^2} - n_3}$$

where

D=a diameter of the fiber $n_2$=a refractive index of a curved distal end core $n_3$=a refractive index of a material surrounding the curved distal end core NA=The maximum NA of light entering the linear section of the optical fiber.

5. The optical delivery system of claim 1, wherein the bend is elliptical.

6. The optical delivery system of claim 1, wherein the bend is parabolic.

7. The optical delivery system of claim 1, wherein at least 90% of the output beam is delivered in the defined lateral direction.

8. The optical delivery system of claim 1, wherein the optical fiber is made of glass.

9. The optical delivery system of claim 1, wherein the optical fiber has a diameter of from 100 to 1000 microns.

10. The optical delivery system of claim 1, wherein the linear section of the optical fiber and the curved distal end are graded index fibers.

11. The optical delivery system of claim 1, wherein the linear section of optical fiber and the curved distal end are step index fibers.

12. The optical delivery system of claim 1, wherein the linear section of optical fiber and the curved distal end are fiber bundles.

13. The optical delivery system of claim 1, wherein the linear section and the curved distal end are two pieces that are spliced together with an index matching material.

14. The optical delivery system of claim 13, wherein the linear section and the curved distal end are made of the same material.

15. The optical delivery system of claim 14, wherein the linear section and the curved distal end are made of glass.

16. An optical delivery system, comprising:

a light source producing an output beam of light;

an optical fiber coupled to the light source to receive the output beam of light, the optical fiber including a linear section defining a longitudinal axis, and a curved distal end with a distal output tip, the curved distal end having a numerical aperture that is 0.2 or greater than a numerical aperture of the output beam entering the curved distal end, the optical fiber delivering substantially all of the output beam to a treatment site in a defined lateral direction from the longitudinal axis at the distal output tip.

17. The optical delivery system of claim 16, wherein the light source is a laser.

18. The optical delivery system of claim 16, wherein the light source is an incoherent light source.

19. The optical delivery system of claim 16, wherein at least 90% of the output beam is delivered in the defined lateral direction.

20. The optical delivery system of claim 16, wherein the optical fiber is made of glass.

21. The optical delivery system of claim 16, wherein the optical fiber has a diameter of from 100 to 1000 microns.

22. The optical delivery system of claim 16, wherein the linear section of the optical fiber and the curved distal end are graded index fibers.

23. The optical delivery system of claim 16, wherein the linear section of the optical fiber and the curved distal end are step index fibers.

24. The optical delivery system of claim 16, wherein the linear section of the optical fiber and the curved distal end and a fiber bundle.

25. The optical delivery system of claim 16, wherein the linear section and the curved distal end are two pieces that are spliced together.

26. The optical delivery system of claim 25, wherein the linear section and the curved distal end are made of the same material.

27. The optical delivery system of claim 26, wherein the linear section and the curved distal end are made of glass.

28. The optical delivery system of claim 16, wherein the numerical aperture of light in the linear fiber section is less than or equal to 0.4, and the numerical aperture of the optical fiber and the curved distal end have a numerical aperture grater than 0.8.

29. The optical delivery system of claim 16, wherein a high numerical aperture curved distal end is spliced to a lower numerical aperture linear fiber section.

30. The optical delivery system of claim 16, wherein linear fiber section is coated with a cladding and the curved distal end is coated with a material of lower refractive index than the cladding of the linear fiber section.

31. The optical delivery system of claim 16, wherein the optical fiber is coated with a cladding, and at least a portion of the curved distal end is uncoated, with the curved distal end being positioned in a sealed hollow tube filled with a gas.

* * * * *